United States Patent [19]

Lando et al.

[11] Patent Number: 5,874,076
[45] Date of Patent: Feb. 23, 1999

[54] ADMINISTRATION OF NON-GLYCOSYLATED, RECOMBINANT HUMAN $IL_2$ IN REDUCED FORM

[75] Inventors: Danielle Lando, Paris; Philippe Riberon, Nogent Sur Marne; Pierre Yves Abecassis, Paris, all of France

[73] Assignee: Roussel Uclaf, France

[21] Appl. No.: 544,092

[22] Filed: Oct. 17, 1995

Related U.S. Application Data

[62] Division of Ser. No. 204,650, Mar. 1, 1994, abandoned, which is a continuation of Ser. No. 869,803, Apr. 16, 1992, abandoned, which is a continuation of Ser. No. 384,986, Jul. 24, 1989, abandoned.

[30] Foreign Application Priority Data

Jul. 28, 1988 [FR] France .................................. 88-10184

[51] Int. Cl.$^6$ .................................................. A61K 38/20
[52] U.S. Cl. .............................. 424/85.2; 514/2; 530/351
[58] Field of Search ................................ 514/2; 530/351; 424/85.2

[56] References Cited

U.S. PATENT DOCUMENTS

| 4,518,584 | 5/1985 | Mark et al. ................................. 424/85 |
| 4,569,790 | 2/1986 | Koths et al. ........................ 260/112 R |
| 4,604,377 | 8/1986 | Fernandes et al. . |
| 4,654,830 | 3/1987 | Yasushi et al. .......................... 530/351 |
| 4,690,915 | 9/1987 | Rosenberg ................................... 514/2 |
| 5,614,185 | 3/1997 | Koths et al. ........................... 424/85.2 |
| 5,643,566 | 7/1997 | Hanisch et al. ........................ 424/85.2 |

OTHER PUBLICATIONS

Weir et al.. (Biochem J. 245: 85–92, 1987).
Robb et al.. (PNAS 80: 5990–94, 1983).
Yamada et al. 1987, (Arch. Biochem Biophys 257, 194).

*Primary Examiner*—Stephen Walsh
*Attorney, Agent, or Firm*—Bierman, Muserlian and Lucas

[57] ABSTRACT

A biologically active, non-glycosylated recombinant human Interleukin 2 (R-$hIL_2$) in reduced form, process for its preparation and method of use.

4 Claims, 10 Drawing Sheets

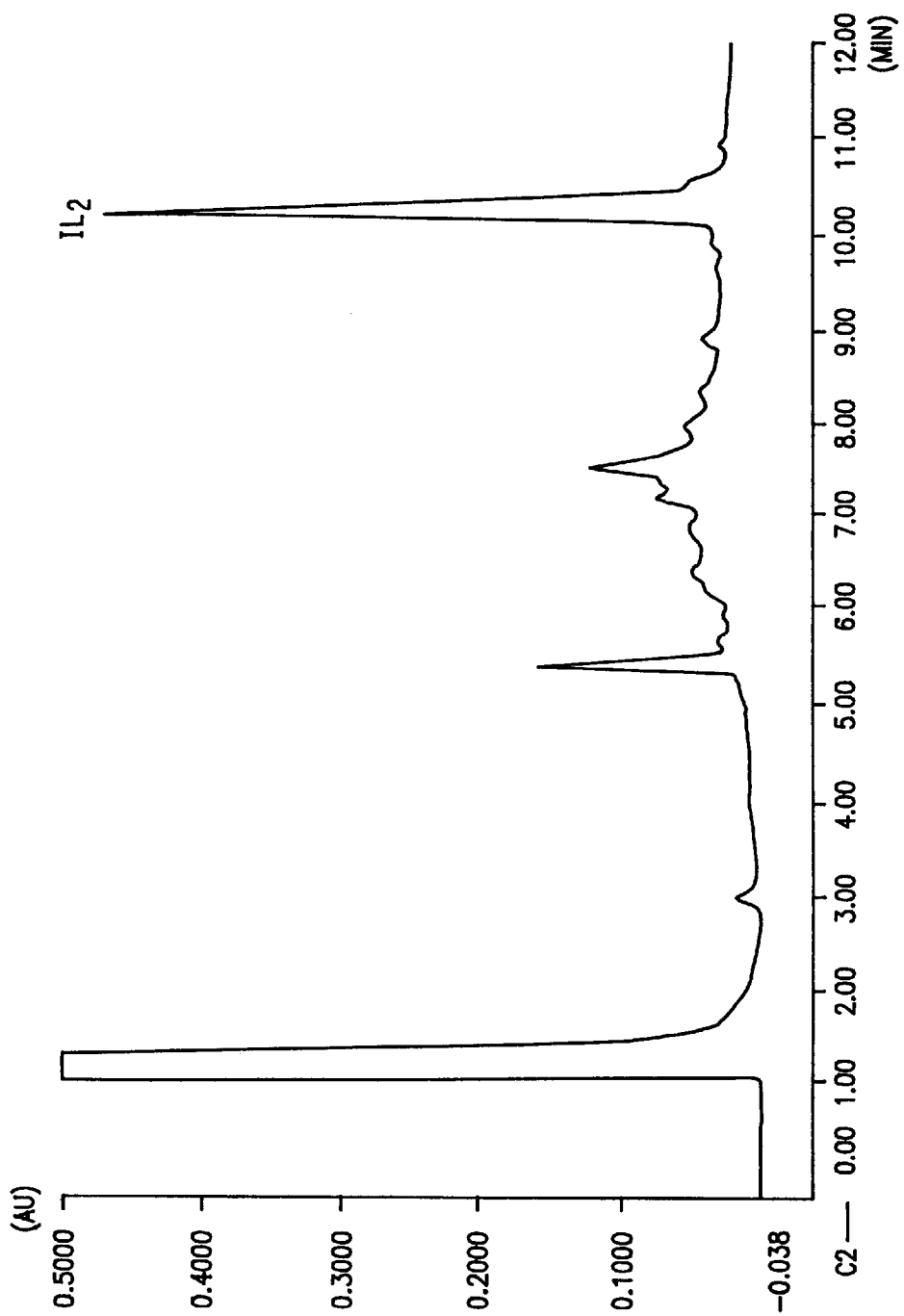
FIG. IA

FERMENTATION

BACTERIA RESIDUE

EXTRACTION

DEFROSTED BACTERIA CONCENTRATE
    MANTOM GUALIN IN WATER
    WASHING IN GUANIDINE
    EXTRACTION IN GUANIDINE
    PRECIPITATION BY DILUTION OF THE GUANIDINE
    WASHING WITH WATER/TFA
    RESOLUBILIZAION BY ACETONITRILE/TFA

CHROMATOGRAPHY

RP-HPLC C4 GRADIENT ACETONITRILE/TFA
    COOLING TO −20°C
    RP-HPLC C4 GRADIENT ISOPROPANOL/CITRIC ACID
    ELIMINATION OF THE ISOPROPANOL BY DISTILLATION IN A VACUUM

LYOPHILISATION

ADMINISTRATION OF NON-GLYCOSYLATED, RECOMBINANT HUMAN IL₂ IN REDUCED FORM

PRIOR APPLICATION

This application is a division of U.S. patent application Ser. No. 204,650 filed Mar. 1, 1994 which is a continuation of U.S. patent application Ser. No. 869,803 filed Apr. 16, 1992 which is a continuation of U.S. patent application Ser. No. 384,986 filed Jul. 24, 1989, all now abandoned.

STATE OF THE ART

Natural human $IL_2$ which is a lymphokine stimulating the proliferation of activated T cells, has 3 cysteines localized at position 58, 105 and 125 in the amino acid sequence of the protein. The cysteines at position 58 and 105 are joined by a disulfide bridge whereas the cysteine at position 125 has a free sulfhydryl group (Cobb et al., Proc. Natl. Acad. Sci. (1984), Vol. 81 page 6486–6490).

The processes for the preparation of human $IL_2$ alleles or derivatives, by the technology of recombinant DNA are described. For example, Taniguchi et al., Nature (1983) 302 305–310 and Devos et al., Nucleic Acids Research (1983) Vol. 11, page 4307–4323 have described the cloning of the human $IL_2$ gene and its expression in micro-organisms, and Ju et al., J. Diol. Chem (1987) Vol. 262 p. 5723–5731 have obtained the expression of recombinant derivatives of $IL_2$.

It is known that when $IL_2$ is accumulated in a microorganism in a state of insoluble granules, it is found in reduced form containing 3 thiol groups and is void of activity (Japanese Patent Application J6 1,257,931). It was therefore admitted that to have available an active $IL_2$ there had to be an oxidation process of the reduced protein accumulated in the granules. To do this, after dissolving the protein in a denaturizing medium, the formation of a suitable disulfide bridge 58–105 which needs renaturization, was carried out in a controlled oxidizing medium. Different methods have been described such as oxidation by oxygen alone (autooxidation in air) or in the presence of cupric ions, or of a weak oxidant such as a thiol or by a thiol-disulfide mixture. (Tsuji, T et al., Biochemistry (1987) Vol. 26 p. 3129–3134).

After oxidative renaturization, purification by chromatography is necessary to eliminate the oxidation products corresponding to the formation of isomeric intramolecular bridges 58–125 and 105–125 as well as the intramolecular bridges which have been shown to be inactive and can be separated by inverse phase chromatography according to Wang et al., Science (1984) Vol. 224, p 1431–1433 or Browing et al., Anal. Biochem. (1986) Vol. 155, p 123–128).

Obtaining homogeneous oxidized recombinant $IL_2$ having suitable biological activity, starting from the accumulated protein in the form of granules, therefore raises certain technical problems) whatever the process used because several purification steps are needed which leads to a lower yield of the desired product.

Two other references which relate to $IL_2$ can be cited: European Patent EP 0145390 and U.S. Pat. No. 4,738,927.

OBJECTS OF THE INVENTION

It is an object of the invention to provide novel non-glycosylated, recombinant human Interleukine 2 in reduced form and a process for its preparation without reoxidation.

It Is another object of the Invention to provide novel immunomodulating compositions and method.

These and other objects and advantages of the invention will become obvious from the following detailed description.

THE INVENTION

One aspect of the invention relates to non-glycosylated, recombinant human Interleukine 2 having the following sequence of amino acids:

X-Ala Pro Thr Ser Ser Ser Thr Lys Lys Thr Gln Leu Gln Leu
    Glu His Leu Leu Leu Asp Leu Gln Met Ile Leu Asn Gly
    Ile Asn Asn Tyr Lys Asn Pro Lys Leu Thr Arg Met Leu
    Thr Phe Lys Phe Tyr Met Pro Lys Lys Ala Thr Glu Leu
    Lys His Leu Gln Cys Leu Glu Glu Glu Leu Lys Pro Leu
    Glu Glu Val Leu Asn Leu Ala Gln Ser Lys Asn Phe His
    Leu Arg Pro Arg Asp Lou Ile Ser Asn Ile Asn Val Ile Val
    Leu Glu Leu Lys Gly Ser Glu Thr Thr Phe Met Cys Glu
    Tyr Ala Asp Glu Thr Ala Thr Ile Val Glu Phe Leu Asn Arg
    Trp Ile Thr Phe Cys Gln Ser Ile Ile Ser Thr Leu Thr as well as the allels or derivatives of this sequence in which X is methionine or hydrogen and the three cysteines at position 58, 105 and 125 are in reduced form, and having a biological activity comparable to that of oxidized $IL_2$ having the same sequence and containing a disulfide bridge at position 58–105.

By alleles and derivatives, the sequences of one or more amino acids other than cysteines 58,105 and 125, modified by substitution, deletion or addition are included, to the extent that these products keep the biological activity characteristic of reduced $IL_2$. Obtaining such modifications is well known in the method of recombinant DNA, for example by the guided mutagenesis techniques reviewed by Lather et al in Genetic Engineering Academic Press (1983) 31–50 or Smith et al., Genetic Engineering Principals and Methods, Plenum Press (1981) 3 1–32.

By reduced form, it is understood that the cysteine residues, which $IL_2$ contains, have a free sulfhydryl group, the determination of which is, for example, carried out by spectro-photometry with dithiodipyridine as the thiol reagent. The biological activity of the reduced form dealt with in the invention is determined, similar to that of the corresponding oxidized form containing the disulfide bridge 58–105, by measure ment of the proliferation of the leukemic cellular lines of mice depending on $IL_2$ CT11-2, with a colorimetric test with tetrazolium salt (Mossmann, T J. Immunol Meth. (1983) Vol. 65, p 55–63).

The invention also relates to a non-glycosylated, recombinant human $IL_2$ having the following sequence of amino acids:

X-Ala Pro Thr Ser Ser Ser Thr Lys Lys Thr Gln Leu Gln Leu
    Glu His Lou Lou Lou Asp Leu Gln Met Ile Lou Asn Gly
    Ile Asn Asn Tyr Lys Asn Pro Lys Lou Thr Arg Met Leu
    Thr Phe Lys Phe Tyr Met Pro Lys Lys Ala Thr Glu Lou
    Lys His Leu Gln Cys Leu Glu Glu Glu Leu Lys Pro Lou
    Glu Glu Val Lou Asn Leu Ala Gln Ser Lys Asn Phe His
    Leu Arg Pro Arg Asp Lou Ile Ser Asn Ile Asn Val Ile Val
    Leu Glu Leu Lys Gly Ser Glu Thr Thr Phe Met Cys Glu
    Tyr Ala Asp Glu Thr Ala Thr Ile Val Glu Phe Leu Asn Arg
    Trp Ile Thr Phe Cys Gln Ser Ile Ile Ser Thr Lou Thr as well as the allels or derivatives of this sequence in which X is methionine or hydrogen and the three cysteines at position 58, 105 and 125 are in reduced form, and having a biological activity of at least $0.5 \times 10^7$ U/mg. The unit of $IL_2$ activity is defined as the quantity which produces 50% of the maximum response in the Lest. A sample "Biological Response Modifier Program (BRMP) reference human reagent $IL_2$(Jurkat)" provided by the the National Cancer Institute (NCI) is used as a standard.

More precisely, the invention relates to non-glycoslated, recombinant human interleukine 2 having the following sequence of amino acids:

X-Ala Pro Thr Ser Ser Ser Thr Lys Lys Thr Gln Leu Gln Leu
    Glu His Leu Leu Leu Asp Leu Gln Met Ile Leu Asn Gly

Ile Asn Asn Tyr Lys Asn Pro Lys Leu Thr Arg Met Leu
Thr Phe Lys Phe Tyr Met Pro Lys Lys Ala Thr Glu Leu
Lys His Lou Gln Cys Leu Glu Glu Glu Leu Lys Pro Lou
Glu Glu Val Lou Asn Leu Ala Gln Ser Lys Asn Phe His
Lou Arg Pro Arg Asp Lou Ile Ser Asn Ile Asn Val Ile Val
Leu Glu Leu Lys Gly Ser Glu Thr Thr Phe Met Cys Glu
Tyr Ala Asp Glu Thr Ala Thr Ile Val Glu Phe Lou Asn Arg
Trp Ile Thr Phe Cys Gln Ser Ile Ile Ser Thr Lou Thr in which X is methionine or hydrogen and the three cysteines at position 58,105 and 125 are in reduced form and having biological activity similar to that of natural human $IL_2$.

By similar activity it is understood the same specific activity as that of natural $IL_2$ isolated from the leukemic Jurkat cells, that is to say $1.3 \times 10^7$ U/mg (reference BRMP), or an activity differing at the most by 25% of this specific activity. The sequence of reduced $IL_2$ dealt with in the invention optionally has a supplementary N-terminal methionine according to the transformed micro-organism, such as *E. coli*, in which it is expressed. In a preferred embodiment of the invention, the sequence containing methionine is prefered, but a mixture of a product containing methionine with a product which does not contain methionine or the product which is deprived of methionine can also be used.

Another aspect of the invention relates to a process for the preparation of reduced, non-glycosylated, recombinant human $IL_2$ comprising extracting $IL_2$ accumulated in the form of granules in a transformed micro-organism, by solubilization in a reducing medium with a chaotropic agent, purification by precipitation followed by inverse phase, high performance liquid chromatography with an acid eluant) and characterized in that:

a) if necessary, the principal fraction eluted in the said chromatography is submitted to a cooling stage at a temperature in the range of $-20°$ C., then to separation of the aqueous phase which b) is diluted in an acid medium, then is chromatographed on another inverse phase, high performance liquid chromatography column in an acid medium to obtain the said $IL_2$.

The recombinant $IL_2$ produced in the form of granules, because of the high rate of expression, by a transformed micro-organism such as *E.coli*, can be solubilized by known methods with a concentrated solution of a chaotropic agent such as 6 to 8M, solution of guanidine salt, then purified by inverse phase, high performance liquid chromatography (hereafter called RP-HPLC) with commercially avaiable supports, preferably of grafted silicas such as C3, C4, C8 or C18, with an acid eluant having a pH value between 1 and 4. The $IL_2$ can be eluted from the column by a gradient system comprising an organic acid such as acetic acid or trifluoroacetic acid (hereafter called TFA) and an organic solvent such as acetonitrile. The principal fraction, the elution of which is detected by spectrophotometry at 280 nm, is the raw material for the optional cooling stage which forms part of the process of the present invention.

By cooling, it is understood that the said principal fraction collected at ambient temperature is placed in an environment with a temperature on the order of $-20°$ C.) which allows the progressive formation of a solid aqueous phase, the supernatant fraction of which can be eliminated by decanting. The aqueous phase, optionally separated in such a way, serves, after dilution, as the raw material for the RP-HPLC in the acid medium described below which forms a part of the process of the invention.

The dilution of the aqueous phase is carried out in an acid medium having a ply value of from 1 to 4, and preferably from 2 to 3. The diluted aqueous phase is chromatographed on an inverse phase column using commercially available supports such as grafted silicas C3, C4, C8 or C18 having pores of a suitable size for use with proteins, for example of a diameter of at least 150 A°. The elution of $IL_2$ includes the use of a gradient of increasing concentration of a lower alcohol miscible with water and containing an organic acid.

The process of the invention is notably characterized in that the optional cooling stage is carried out in an aqueous solution of acetonitrile containing approximately 0.1% trifluoroacetic acid, in that the dilution is carried out with an aqueous solution of an organic acid such as citric acid and in that the said $IL_2$ is eluted in the second chromatograph with a solution containing isopropanol, water and an organic acid such as citric acid. The aqueous solution of acetonitrile containing approximately 0.1% of TFA, which is the preferred mixture submitted to the optional cooling stage of the invention, corresponds to the principal fraction eluted in the first chromatography. More preferably, the dilution of the aqueous phase is carried out immediately, either after the optional separation, or after the first chromatography. This dilution is carried out by addition, preferably, of at least 2 volumes of water containing 0.5 to 2% of an organic acid such as formic acid, acetic acid, propionic acid, trifluoroacetic acid or citric acid, more preferably by the addition of approximately 2 volumes of water containing 0.5% of citric acid.

The second chromatograph which forms a part of the process of the invention consists of submitting the aqueous phase, which is optionally separated after the cooling stage and then diluted, to a RP-HPLC using commercially available supports such as grafted silicas C3, C4, C8 or C18 having pore diameters of at least 150° A. The preferred support is a grafted silica C4 VYDAC 300° A which is a silica gel which has butyl groups grafted in covalent manner, of which the pores have a diameter of 300° A and the particles have an average size of 15 to 20 microns.

The elution of $IL_2$ dealt with in the process of the invention is carried out with a gradient system comprising an alcohol such as propanol or isopropanol and an organic acid such as formic acid, acetic acid, propionic acid, trifluoroacetic acid or citric acid. The preferred mixture comprises isopropanol, water and citric acid preferably at 0.5 to 2%, more preferably at 0.5% and allows, with a gradient system of increasing concentrations of isopropanol, the elution of a lower fraction at approximately 48% of isopropanol, then a higher fraction at approximately 59% of isopropanol, this latter comprising non-glycosylated, active recombinant human $IL_2$ in reduced form.

The subject of the invention is also non-glycosylated, recombinant human $IL_2$ in reduced form which can be obtained by the process described above. The said fraction obtained can be kept at approximately 0° to $-20°$ C. as it is stable under these conditions. The isopropanol can also be eliminated by azeotropic distillation in a vacuum. The solution obtained can be kept at $+4°$ C. or the $IL_2$ of the present invention can be isolated immediately by lyophilization.

The invention also relates to a variation of the process in which the principal fraction is not submitted to the cooling stage and separation of the aqueous phase. The diluted principal fraction obtained by this claimed variation of the process can also be kept at $+4°$ C. as it is stable and constitutes the raw material for the second chromatography which forms part of the process of the invention.

When the thiol groups are measured, the $IL_2$ obtained by the invention has 3 free sulfhydryl groups and shows a specific activity of 0.7 to $1.3 \times 10^7$ U/mg in the proliferation test of the CTLL-2 lines, which is similar to that of natural $IL_2$. This activity justifies the use of the non-glycosylated, recombinant human $IL_2$ in reduced form for use as a medicament in the same manner as natural $IL_2$, in a variety of ways to use its immuno-modulating activity as well as its antitumoral activity which have been described for example by Fletcher et al., Lymphokine Research Vol. 6 (1987) p 47–57 and which comprises, for example, the proliferation of T lymphocytes, the induction of the cytotoxicity of the NK (natural killer) cells and the LAK (lymphokine activated killer) cells, the restoration of cellular immunity, a protective effect against infection in cases of immunity deficiencies or an adjuvant effect with regard to vaccines. The administration can be carried out directly or can be an administration associated with a method of adoptive immuno-therapy which was described by Rosenberg et al., in N. Engl.J. Med. (1985) Vol. 313, p 1485–1492.

As with natural $IL_2$, the $IL_2$ of the invention can be used by itself or with other immuno-modulator agents such as alpha interferon, gamma interferon and/or other therapeutic agents.

The immunomodulating compositions of the invention are comprised of an immunomodulating effective amount of the non-glycosylated recombinant human $IL_2$ in reduced form and an inert pharmaceutical carrier.

The compositions may be formed, for example by removing isopropanol from the above aqueous solutions of the product described above by azetropic distillation under reduced pressure and after the addition of a water-soluble loading agent, the product is lyophilized.

The water-soluble loading agent is a substance which will not change the initial pH when the product is reconstituted and examples are sugars such as glucose, ribose, saccharose, maltose and trehalose and reduced sugars such as mannitol.

Mannitol is preferred and is added at a concentration of from 10 to 50 mg/ml, preferably about 50 mg/ml when the concentration of $IL_2$ of the present invention is between 0.05 and 1 mg/ml, depending on the dose to be administered. The solution is filtered under sterile conditions in the absence of oxygen and divided into dosing flasks and lyophilized. The lyophilized mixture can be reconstituted by injection in the flask of distilled water suitable for parenteral injection.

When the composition is to be used for perfusion administration, it is more particularly characterized in that it contains besides non-glycosylated, recombinant human $IL_2$ in reduced form, water and an organic acid such as citric acid. Such a composition can be obtained starting from the lyophilized pharmaceutical composition of the invention which is dissolved in the presence of an appropriate vehicle which contributes to the stability of the active principle during the time of the perfusion, for example glucose. The preferred conditions consist in diluting the lyophilized mixture reconstituted by injection of distilled water, by introducing it in a perfusion pocket containing a volume of glucose at a concentration of 50 mg/ml determined as suitable for the dose to be administered.

The novel method of the invention for inducing immuno-modulating activity in warm-blooded animals comprises administering to warm-blooded animals an immunomodulating effective amount of the product of the invention. The product may be administered intraveneous route in bolus or continuous perfusion, by intramuscular, intraperitoneal, intrapleural or subcutaneous route. The usual daily dose is depending on the conditions treated, the person concerned, and method of administration. It can be $1.10^6$ U/M$^2$/24 h to $40.10^6$U/M$^2$/24 h, and preferably $20.10^6$U/M$^2$/24 h in the adult or in the child.

BRIEF DESCRITPTION OF DRAWINGS

FIG. 1a is an analytic chromatogram of RP-HPLC of the crude extract in 8M guanidine of Example 1.

FIG. 5 is the purification protocol of Example 1.

EXAMPLE 1

Purified Reduced, Biologically Active r-hIL$_2$ Starting from Granules

Figure 1B:
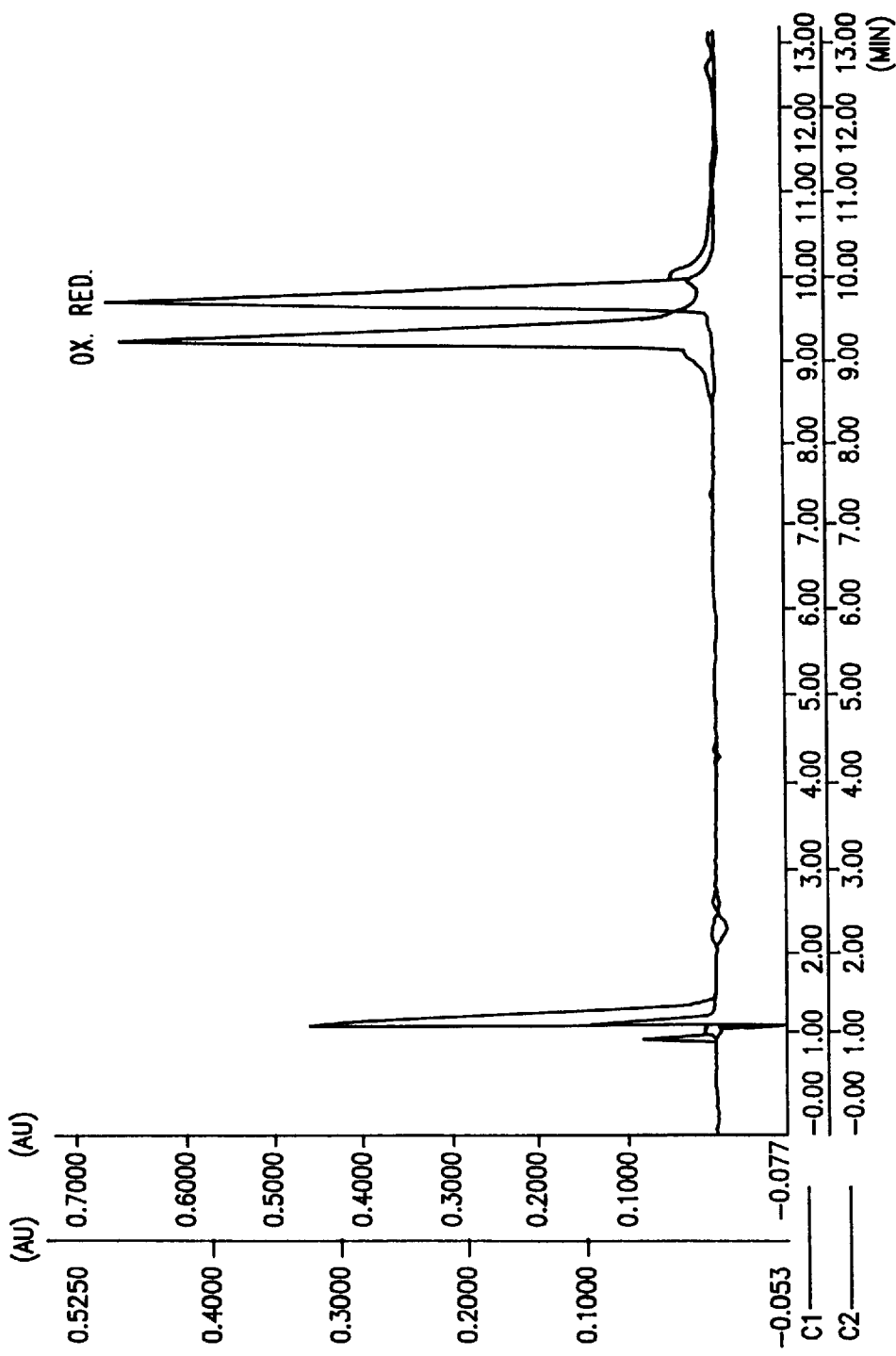
FIG. 1b is an analytic chromatogram of RP-HPLC of the standard reduced and oxidized $IL_2$.
Figure 2:
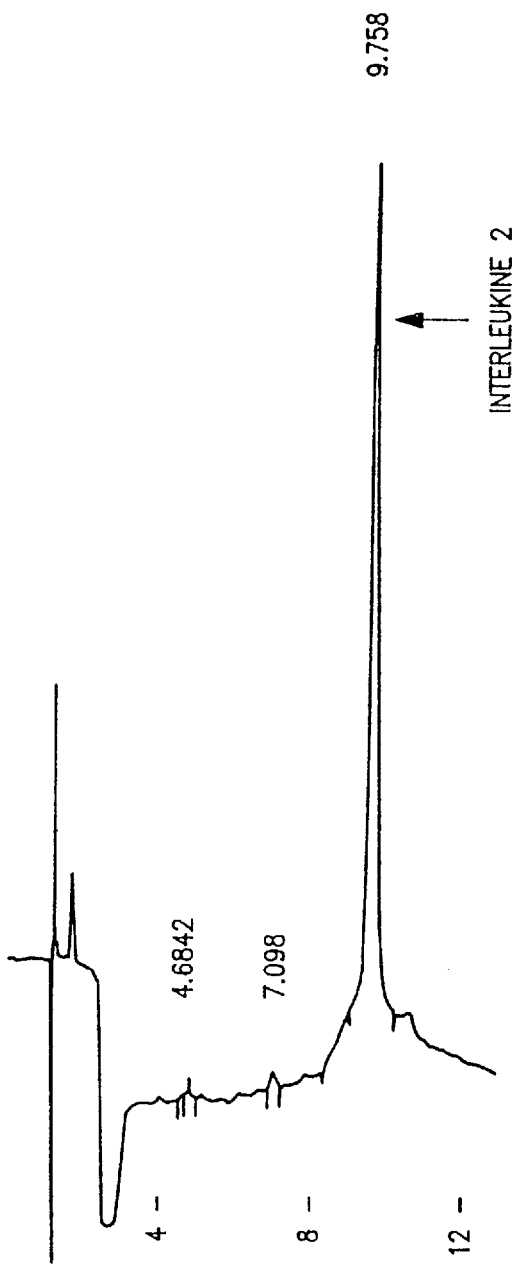
FIG. 2 is an analytic chromatogram of RP-HPLC of the "resolubilization" of Example 1.
Figure 3:
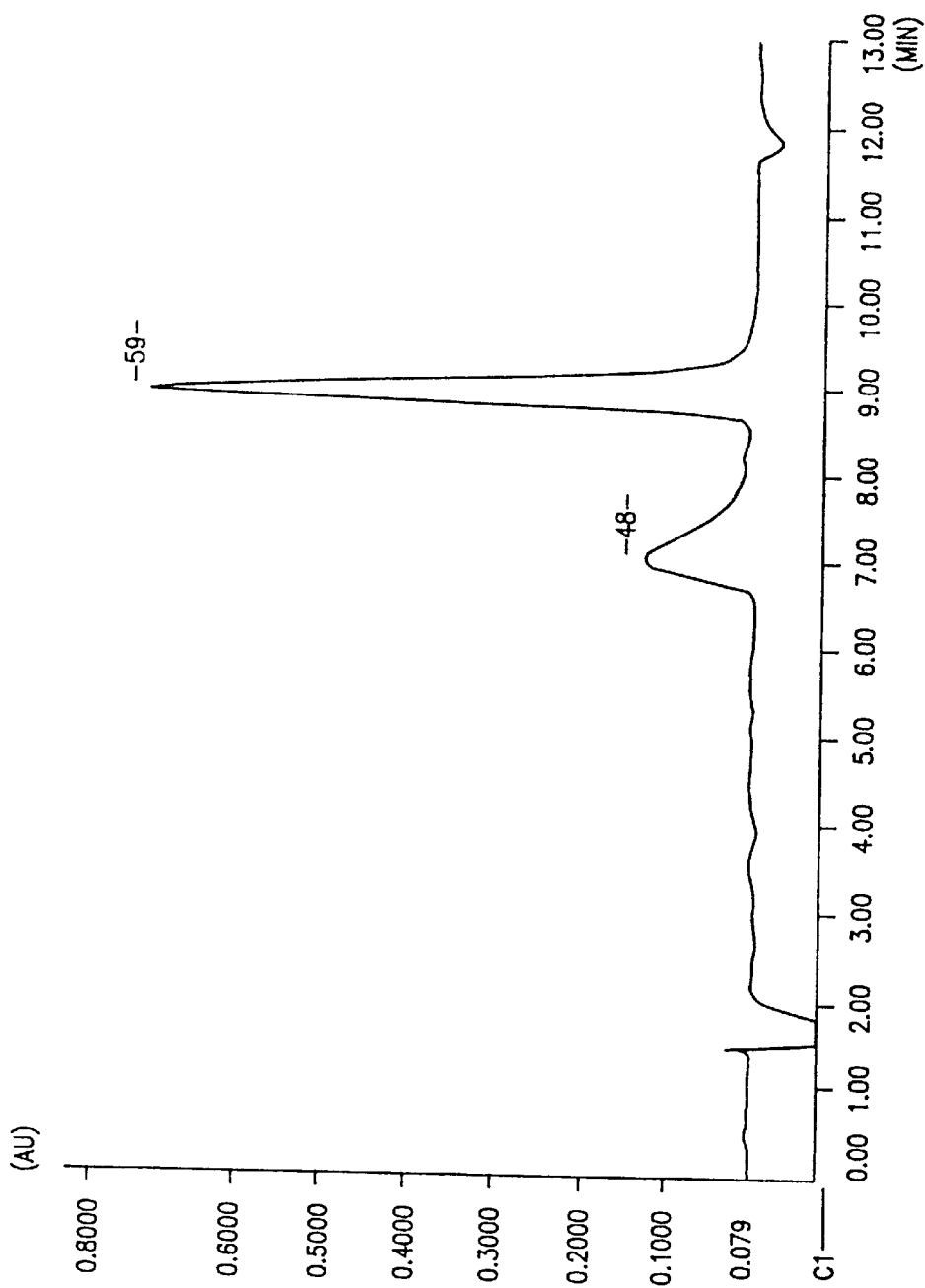
FIG. 3 is a chromatogram of RP-HPLC of the "principal fraction" after the cooling stage of Example 1.

Granules were obtained by centrifuging cultures of an *E.coli* strain transformed by a plasmide containing the coding sequence for natural $IL_2$ and capable of accumulating $IL_2$ in that form in the interio of the cells as described for example by Sato et al., [J. Biochem (1987) Vol. 101 p 525–534]. The cells obtained from a 10 liter fermenter were subjected to an explosion in a Manton Gaulin homogenizer. Starting from isolated and washed cellular residue (90 to 170 g wet weight), the $IL_2$ was solubilized in 2.5 volumes of a Tris buffer, HCL 20 mM, pH 8, containing 8M guanidine hydrochloride (Gu,HCL) and 100 mM dithiothreitol (DTT). The solubilized amount of $IL_2$ (1.5 to 2.5 g) was estimated by analytic RLP-HPLC on a C4 VYDAC column (0.46 * 15 cm) 300° A, 5 microns at a flow of 2 ml/mn, with a linear gradient of acetonitrile (30 to 70% in 10 minutes) containing 0.1% of TFA, a spectrophotometric detection at 280 nm or 210 nm, in which the surface of the peak was evaluated at 280 nm after calibration with a standard $IL_2$ (FIG. 1a and FIG. 1b). The $IL_2$ was then precipitated by lowering the concentration of Gu, HCL to 2M in the presence of DTT. After washing the precipitate with an aqueous solution of FFA at 0.1% until a pH value less than 5.0 was obtained for the supernatant, the $IL_2$ was solubilized in an aqueous solution with 20% of acetonitrile and 0.1% of TFA. The "resolubilization" obtained, which had a content of reduced $IL_2$ greater than 85% according to the analytic RP-HPLC (FIG. 2), had a biological activity lower than $0.01 \times 10^7$ U/mg of reduced $IL_2$ and a content of sulfhydryl groups of 2.85 SH/mole of reduced $IL_2$. One fraction of the solution obtained, corresponding to approximately 200 mg of $IL_2$ estimated by the analytical RP-HPLC, was diluted to adjust the concentration of acetonitrile to less than 10% in TFA at 0.1%, then applied to a C4 VYDAC column (5.7×30 cm). The $IL_2$ was eluted at a flow of 100 ml/mn with a linear gradient of acetonitrile (30 to 80% in 40 minutes) containing 0.1% of TFA, at a concentration; of approximately 60% in acetonitrile in a major peak detected by spectrophotometry at 280 nm and analyzed by RP-HPLC. The "principal fraction" collected which contained the reduced $IL_2$ was then submitted to a slow cooling stage from ambient temperature to $-20°$ C.$\pm 1°$ C which allowed a superior organic phase which was rich in acetonitrile to be eliminated by decanting. The inferior phase, rich in water and containing the $IL_2$, was kept in a frozen state. After thawing, the solution obtained, after dilution by 2 volumes of a 0.5% aqueous solution of citric acid, was applied to a C4 VYDAC column (5.7×30 cm) which was developed with a linear gradient of isopropanol (20×70% in 40 minutes) containing 0.5% citric acid with a flow of 50 ml/mn. The effluent, followed by spectrophotometry at 280 nm, showed the successive elution of a minor peak at a concentration of approximately 48% in isopropanol (fraction "48") and a major peak at a concentration of approximately 59% isopropanol (fraction "59") (FIG. 3). The fraction "59" was collected and it was stable when kept at 0° C. for at least 24 hours and protected from air.

Figure 4:
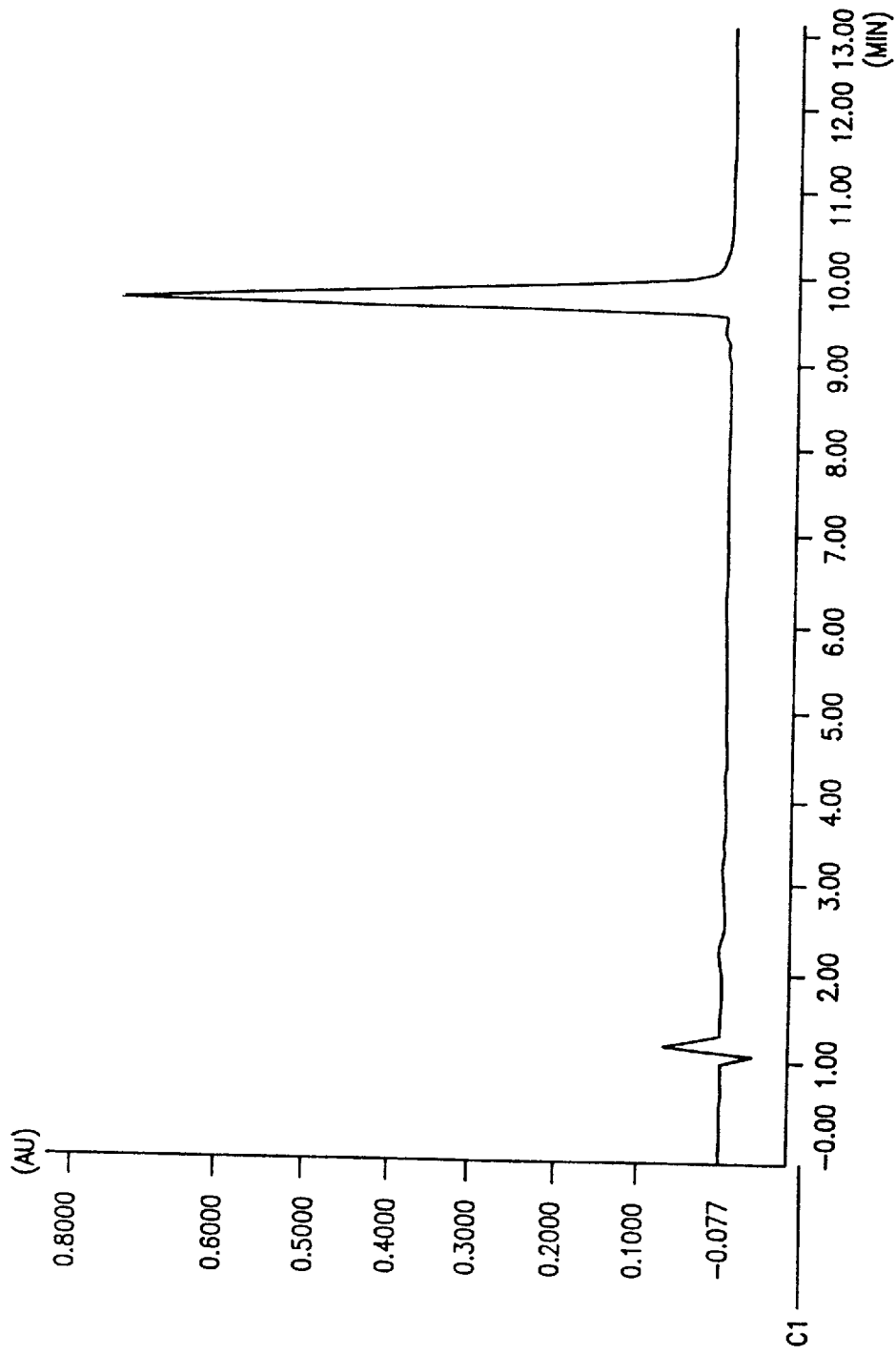
FIG. 4 is an analytic chromatogram of RP-HPLC of the fraction "59" of Example 1.

After elimination of isopropanol by azeotropic distillation in a vacuum, the "59" fraction was analyzed in analytical RP-HPLC and gave a homogeneous peak (FIG. 4) eluted with approximately 60% of acetonitrile whereas the reference oxidated $IL_2$ was eluted at approximately 57% of acetonitrile (FIG. 1b). The "59" fraction which, after elimination of the isopropanol, had a concentration of $IL_2$ greater than 1 mg/ml and a pH value of 3 ±0.5 was kept at +40° C. and protected from air for at least a week or it could be immediately lyophilized or formulated to obtain a pharmaceutical composition. The lyophilized "59" fraction was dosed in biological activity according to the in vitro test of the proliferation of the cells CTLL-2, and had a specific activity of $1.3 \pm 0.5 \times 10^7$ U/mg similar to that of natural $IL_2$.

The content of free sulfhydryl groups of the lyophilized "59" fraction, determined by the colorimetric method with dithiodipyridine, was 2.94 SH/ mole comparative to 0.76 SH/mole for the oxidized reference $IL_2$. 150 to 300 mg titrated by the analytical RP-HPLC of the reduced R-$hIL_2$ containing 3 SH groups, biologically active, homogenous in RP-HPLC, were obtained in the "59" fraction starting from a 10 liter fermenter (according to the protocol scheme FIG. 5).

EXAMPLE 2

Purification of the Biologically Active, Reduced r-$hIL_2$

The procedure of Example 1 was repeated except that the "principal fraction" was not submitted to the cooling stage then to separation by decanting but was diluted immediately by 2 volumes of a 0.5% aqueous solution of citric acid. The "59" fraction was collected and treated as in Example 1.

EXAMPLE 3

Physiochemical Characterization of the Biologically Active Reduced r-$hIL_2$

The reduced r-$hIL_2$ obtained by the invention in the "59" fraction of Example 1 was examined for the following properties:
1) Homogeneity The SDS PAGE electrophoresis was carried out on a gel in two phases (concentration gel and migration gel with 5% and 15% of acrylamide rsepectively) containing 10% of SDS. The sample was first heated for 2 minutes at 100° C. in a buffer with 3% of SDS and 5% of mercaptoethanol. The migration with a buffer at 1% of SDS was followed by coloration by silver which revealed a single band corresponding to a purity higher than 99% for a deposit of 2 ug (FIG. 6).

2) Molecular weight by electrophoresis

Figure 6:
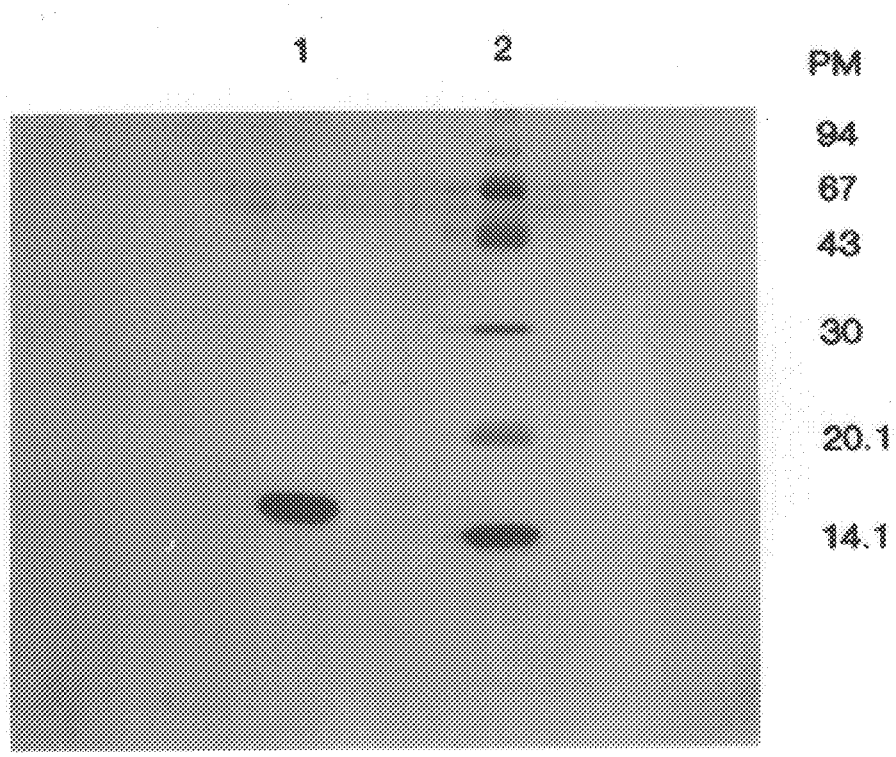
FIG. 6 is the electrophoresis gel SDS-PAGE of Example 2.

In a reducing medium, an apparent MW of approximately 15 Kd was determined in accordance with the calculaed MW of 15420 (FIG. 6).

3) Composition in amino acids

A sample containing 25 ug of the reduced r-$hIL_2$ of the invention in 0.5 ml of water was placed in a glass hydrolysis tube into which 0.5 ml of concentrated hydrochloric acid with 31.7% of TFA and 4.8% of thioglycolic acid were added. The tube was scaled under vacuum and then the hydrolysis was carried out at 155° C. for 40 minutes. The hydrolysate was then evaporated to dryness under reduced pressure. The residue was dissolved ill 0.7 ml of a citrate buffer pH=3 and, then it was submitted to an amino acid analysis on an Interaction AA 511 column (0.46×15 cm) with a pH gradient (3 to 5) and sodium chloride (0 to 70 g/l) in the citrate buffer at 60° C. with a flow of 0.5 ml/mn and a detection by fluorescence, after derivation by orthophtalaldehyde at the column outlet. The results are indicated in Table 1 and the values are the average obtained for 2 repeated hydrolyses and 2 repeated chromatographs respectively. The composition was in agreement with that of natural $IL_2$ having a supplementary N-terminal methionine.

TABLE 1

| | INTERLEUKIN 2 | |
| --- | --- | --- |
| Amino acids | Theoretical number | Number found |
| GLN + GLU | 18 | 17.56 |
| ASN + ASP | 12 | 12.61 |
| THR | 13 | 12.09 |
| SER | 8 | 7.05 |
| PRO | 5 | ND* |
| GLY | 2 | 2.59 |
| AKA | 5 | 5.50 |
| VAL | 4 | 4.34 |
| MET | 5 | 5.59 |
| ILE | 9 | 9.15 |
| LEU | 22 | 19.96 |
| TYR | 3 | 2.60 |
| PHE | 6 | 5.90 |
| TRP | 1 | NC** |
| LYS | 11 | 10.19 |
| HIS | 3 | 3.48 |
| ARG | 4 | 5.29 |
| CYS | 3 | NC** |

*ND = not detected
**NC = not calculated

4) Sequence of N-terminal amino acid

The N-terminal sequence was identified by microsequencing using the Edman automatic degradation method. The analysis of 15 ug of biologically active, r-$hIL_2$ of the invention on a gas phase micro-sequencer Applied Biosystems 470A coupled with HPLC 120A allowed the following PTH amino acids to be identified:

| Stages | PTH AA | Stages | PTH AA |
| --- | --- | --- | --- |
| 1 | Met<br>Ala | 11 | Thr |

-continued

| Stages | PTH AA | Stages | PTH AA |
|---|---|---|---|
| 2 | Ala | 12 | Gln |
|   | Pro |    |     |
| 3 | Pro | 13 | Leu |
|   | Thr |    |     |
| 4 | Thr | 14 | Gln |
|   | Ser |    |     |
| 5 | Ser | 1s | Leu |
| 6 | Ser | 16 | Glu |
| 7 | Ser | 17 | His |
| 8 | Thr | 18 | Leu |
| 9 | Lys | 19 | Leu |
| 10 | Lys | 20 | Leu |

The sequence of the 20 N-terminal residues is in agreement with the theoretical linking order of the natural $IL_2$ and approximately 10% of $IL_2$ without methionine was observed.

5) Peptide chart with cyanogen bromide

Figure 7A:
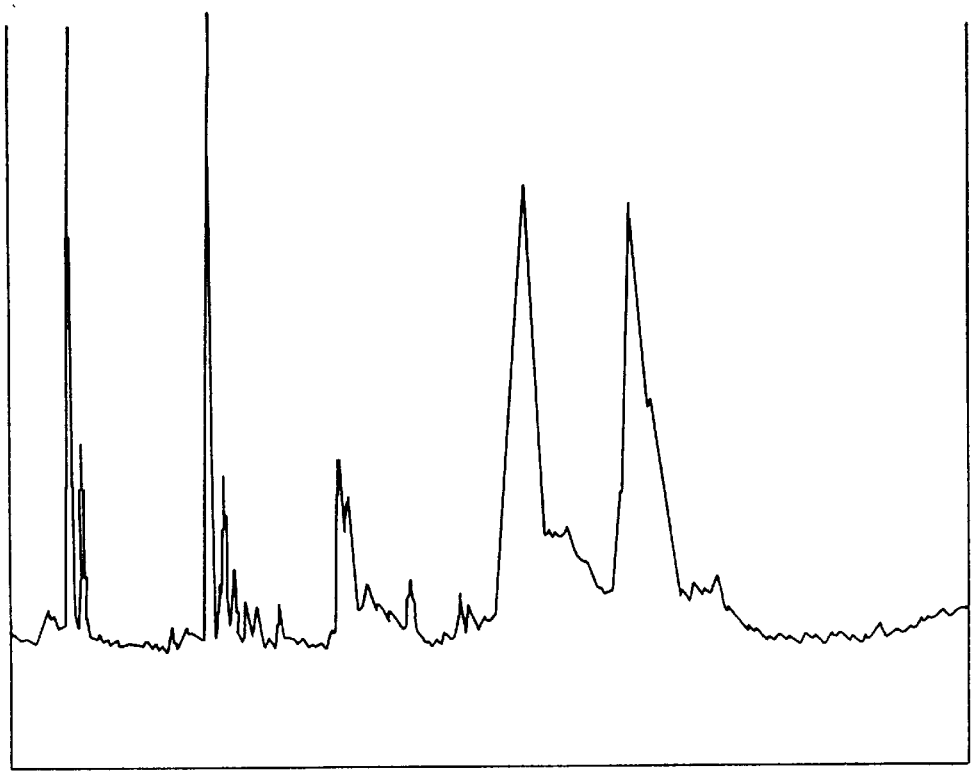
FIGS. 7a and 7b are peptide charts of Example 2.
Figure 7B:
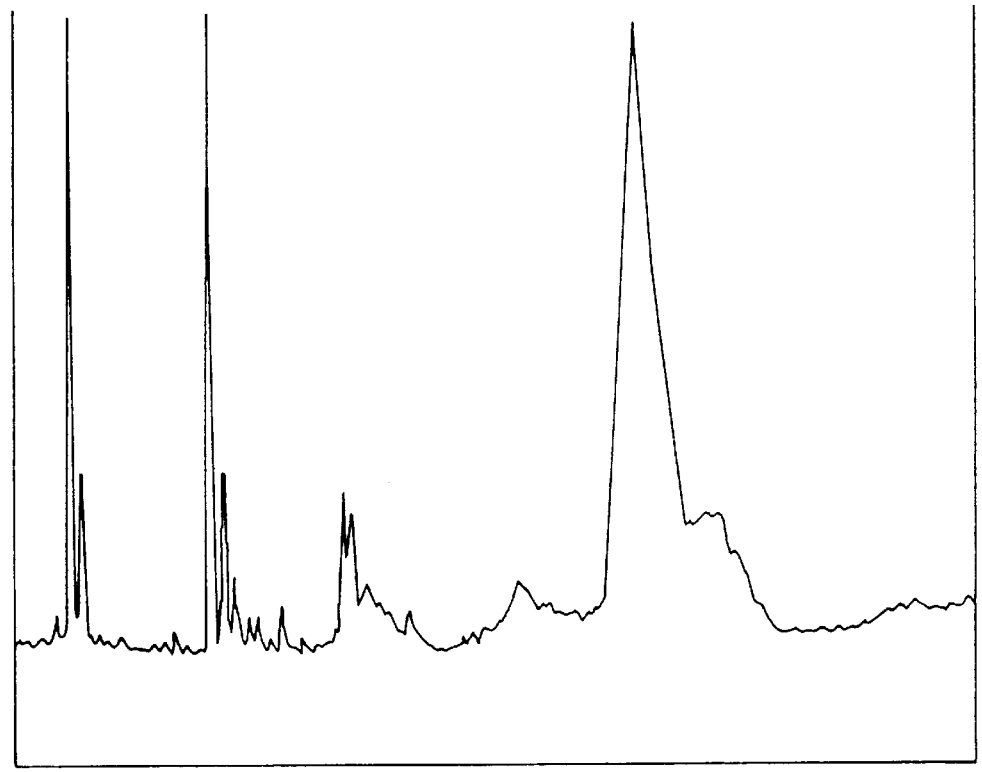

700 μg of reduced $IL_2$ residue of the invention (approximately 53 nmoles) were dissolved in 4 ml of 70% formic acid and 5.6 mg of cyanogen bromide were added. The solution was stirred overnight at ambient temperature, diluted with water, then lyophilized. The reaction mixture was analyzed by RP-HPLC on a uBondapack C18 RP column (0.46×20 cm), with a concentration gradient of acetonitrile varying from 0 to 70% containing 0.1% of TFA with a flow of 1 mil/mn at ambient temperature and with a spectrophotometric detection at 220 nm. The peptide chart of the reduced $r\text{-}hIL_2$ (FIG. 7a) showed a different fragmentation to that of the reference oxidized $IL_2$ (FIG. 7b).

6) Circular dichroism

The circular dichroism spectra (CD) were determined at ambient temperature on a Jobin Yvon Mark V spectrograph. The sample of reduced $r\text{-}hIL_2$ lyophilized after RP-HPLC carried out with a linear gradient of isopropanol in which the 0.5% citric acid according to Example 1 was replaced by formic acid at 0.1%, then distillation of the isopropanol and lyophilization, was taken up at a concentration of 1 mg/ml in acetic acid. The containers used were of 0.01 cm and 0.5 cm respectively for the peptide region (185–250 nm) and the aromatic region (260–320 nm) The solvent spectrum was subtracted from the spectrum of the $IL_2$ for each sample. The results are given in ellipticity 0 (average weight per residue of $IL_2$=116).

Figure 8A:
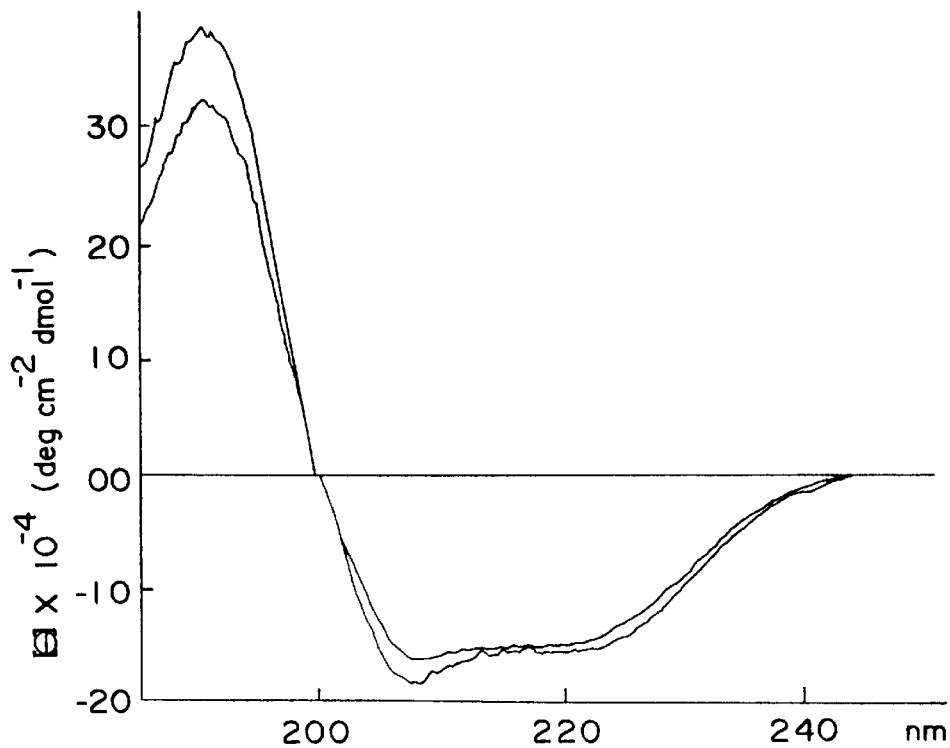
FIGS. 8a and 8b are the curves DC of Example 2.
Figure 8B:
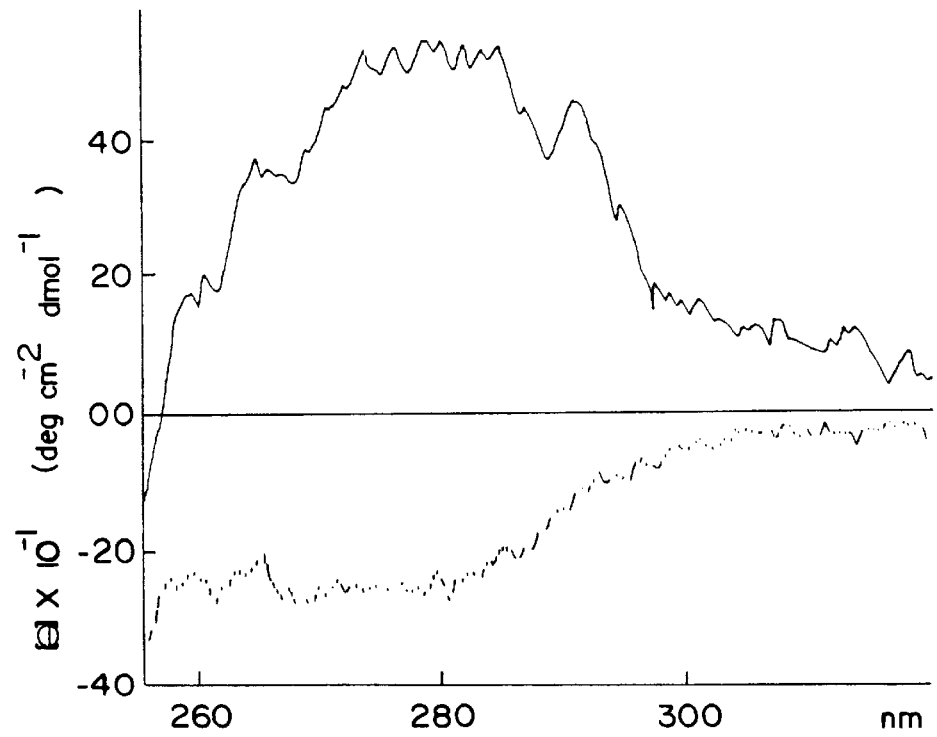

FIG. 8a shows the CD spectrum in distant UV and the reduced biologically active $r\text{-}hIL_2$ of the invention, had a spectrum which indicated the presence of an ordered secondary structure. The determination of the alpha helix % showed little significant difference with the oxidized reference $IL_2$ (% alpha helix ‖50%). FIG. 8b showed the CD spectrum in near UV and the oxidized reference $IL_2$ had a significant DC which indicated an asymetric environment for the aromaic residues, whereas the reduced $r\text{-}hIL_2$ of the invention had a CD of little significance but different.

EXAMPLE 4
Biological Activity

The biological effectiveness of the reduced $r\text{-}hIL_2$ of the invention was evaulated in the in vitro or ex vivo experiments.

1) In vitro activity on human cells a. Lymphoblastic transformation test

Figure 9:
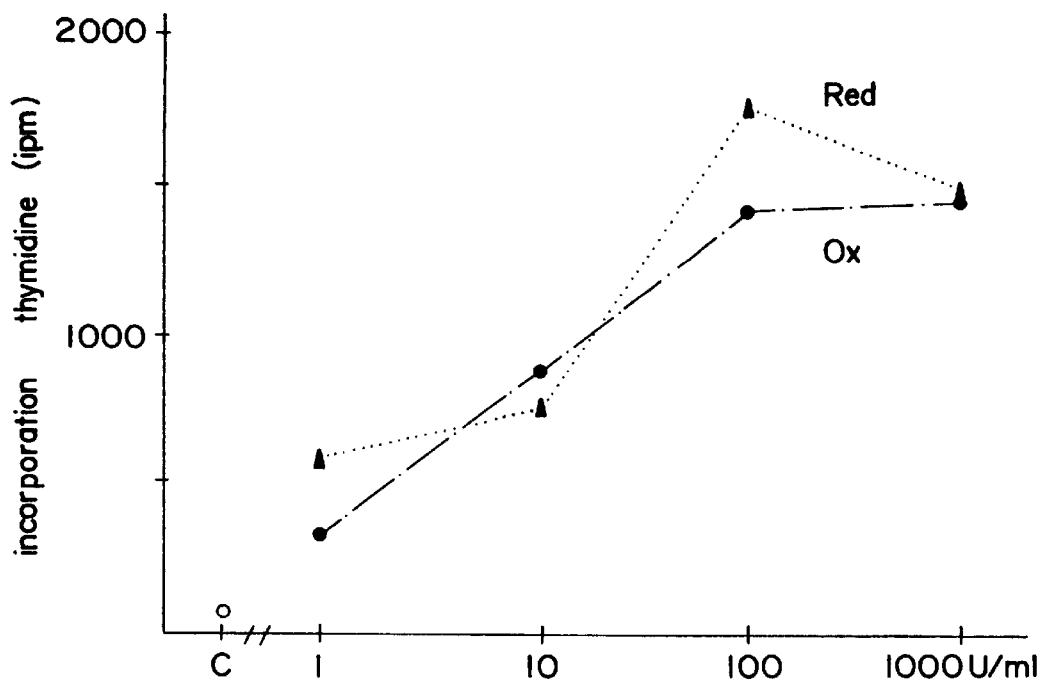
FIG. 9 is the curve of mitogenetic effect on the human lymphocytes of Example 3.

Apart from the proliferative activity on cellular lines of mice such as CTLL-2 which allowed the biological measurement of $IL_2$, the reduced $r\text{-}hIL_2$ of the invention showed a mitogenetic effect, dependent on the dose, similar to that shown by the oxidized reference $IL_2$ on normal circulating human lymphocytes, shown by the measurement of the incorporation of the tritiated thymidine in ADN (FIG. 9).

b. The induction of the cytotoxicity of the mono-nuclear cells

Figure 10:
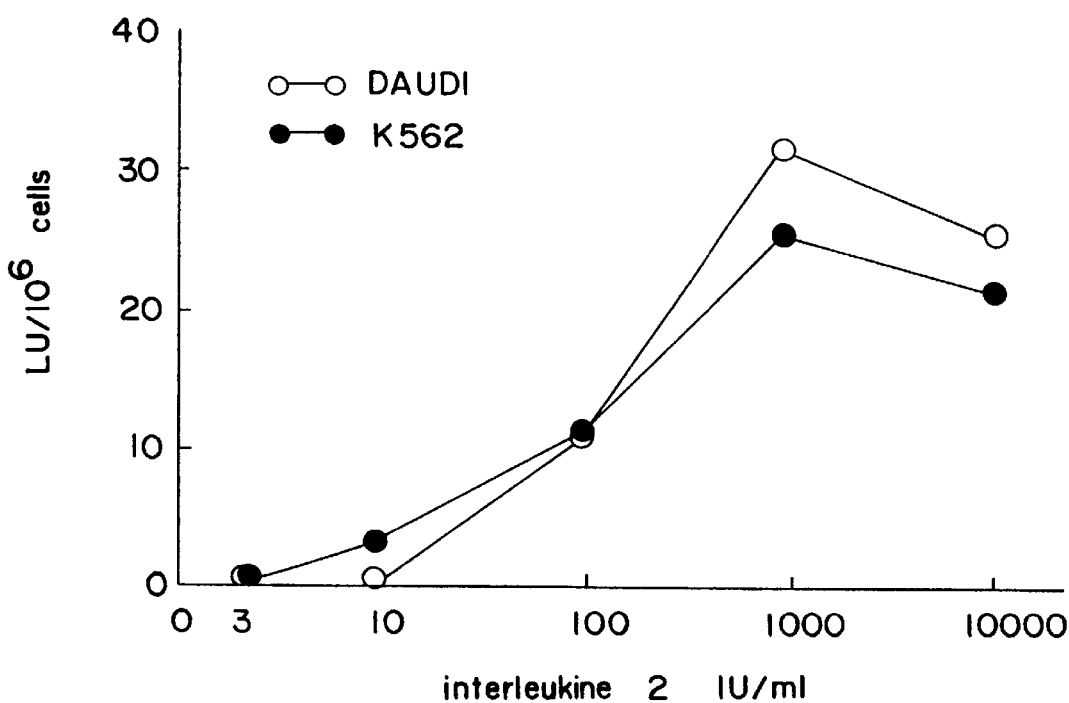
FIG. 10 is the toxicity curve obtained with regard to the lines K 562 and DAUDI, In the following examples there are described several preferred embodiments to illustrate the invention. However, it should be understood that the invention is not intended to be limited to the specific embodiments.

The study is carried out with human circulating mono-nuclear cells incubated in the presence of $IL_2$ and of which the cytotoxic effect was determined with regard to tumoral target cells, the erythroleukemic line K 562 (sensitive to NK cells) and the DAUDI line derived from a B lymphome (resistant to NK cells) respectively, by measuring the salting out of CR 51 in 4 hours. The results, expressed in lytic units per $10^6$ cells ($UL/10^6$), showed that the reduced $r\text{-}hIL_2$ of the invention shows a capacity depending on the dose, to increase the activity of NK or to induce the cytotoxicity of the T lymphocytes with regard to the tumoral targets respectively, in a manner similar to that known for natural $IL_2$ (FIG. 10).

2) Ex vivo activity on mice (stimulation of the peritoneal macrophages)

In normal Balb/c and MRL-+/+ mice, the successive intraperitoneal injections of recombinant interferon gamma of the rat in sub-optimal doses (100 to 3000 U), then 24 hours later, of reduced $r\text{-}hIL_2$ of the invention, released the oxidative mechanisms of the phagocyte cells, evaluated by measuring the chemiluminescence in the presence of phorbal ester (PMA) of the cells removed from the peritoneal cavity of the mice killed 24 hours after the $IL_2$ injection. The effect, depending on the dose, was similar to that seen with the oxidized reference $IL_2$ The results are reported in the following Table.

| Injected dose | Chemiluminescence (CPM × $10^4$) After injection of $r\text{-}hIL_2$ | |
|---|---|---|
| (ng per mouse) | Reduced | Oxidized |
| 0 | 5 ± 2 | 4 ± 3 |
| 1 | 7 ± 3 | 5 ± 1 |
| 3 | 90 ± 5 | 71 ± 5 |
| 10 | 130 ± 10 | 140 ± 70 |
| 30 | 350 ± 50 | 400 ± 70 |
| 100 | 710 ± 20 | 695 ± 25 |
| 300 | 375 ± 25 | 350 ± 20 |

EXAMPLE 5

Pharmaceutical Composition for Injection

The aqueous solution of reduced $r\text{-}hIL_2$ corresponding to the "59" fraction of the invention, from which the isopropanol had been eliminated by azeotropic distillation in a vacuum, was extemporaneously diluted with an aqueous solution of mannitol degassed and saturated with nitrogen at the rate of 100 μg of reduced $IL_2$ ml and 50 mg/ml of mannitol. After filtration on a 0.22 u membrane, sterile distribution of 1 ml in flasks and lyophilization, the flask-doses were stoppered in a nitrogen atmosphere and kept at a temperature of +4° C. before use.

EXAMPLE 6

Pharmaceutical Composition by Continuous Perfusion

The aqueous solution of reduced $r\text{-}hIL_2$ corresponding to the "59" fraction of the invention from which the isopropanol had been eliminated by azeotropic distillation in a vacuum was extemporaneously diluted with an aqueous solution of mannitol degassed and saturated with nitrogen at the rate of 500 ug of reduced $IL_2$/ml and 50 mg/ml of mannitol. After filtration on a 0.22 u membrane) sterile distribution into 1 ml flasks and lyophilization, the flask doses were stoppered under a nitrogen atmosphere and kept at a temperature of 4° C. until use. The contents of each flask was then dissolved by injection of 1 ml of sterile distilled water and the solutions corresponding to 7 flask doses (approximately $35.10^6$ units) were introduced in a Viaflex$^R$ container containing 500 ml of solution for Travenol$^R$ glucose at 5% perfusion.

Various modifications of the compositions and method of the invention may be made without departing from the spirit or scope thereof and it should be understood that the invention is intended to be limited only as defined in the appended claims.

What we claim is:

1. A method of inducing immuno-modulating activity in warm-blooded animals comprising administering to warm-blooded animals an immuno-modulatorily effective amount of a non-glyclosylated, recombinant human $IL_2$ in reduced form obtained by the process of extracting $IL_2$ accumulated in the form of granules in a transformed microorganism by solubilization in a reducing medium with a chaotropic agent, then purifying by precipitation followed by inverse phase high performance liquid chromatography with an acid eluant, and wherein a) optionally submitting the principal fraction eluted from the chromatography to a cooling stage to a temperature on the order of −20° C. and recovery of the aqueous phases b) diluting the aqueous phase in an acid medium and c) subjecting the latter to chromatography on another inverse phase high-performance liquid chromatography column in an acid medium to obtain said $IL_2$ wherein said $IL_2$ in reduced form has a biological activity of $1.3\pm0.5\times10^7$ u/mg.

2. The method of claim 1 wherein the IL-2 is administered as an aqueous solution containing an organic acid.

3. The method of claim 2 wherein the organic acid is citric acid.

4. The method of claim 2 wherein the aqueous solution also contains mannitol.

* * * * *